(12) United States Patent
Davis

(10) Patent No.: US 11,925,791 B2
(45) Date of Patent: *Mar. 12, 2024

(54) SYRINGE PLUNGER WITH HINGED FLANGE

(71) Applicant: Avent, Inc., Alpharetta, GA (US)

(72) Inventor: Benjamin M. Davis, Woodstock, GA (US)

(73) Assignee: Avent, Inc., Alpharetta, GA (US)

(*) Notice: Subject to any disclaimer, the term of this patent is extended or adjusted under 35 U.S.C. 154(b) by 191 days.

This patent is subject to a terminal disclaimer.

(21) Appl. No.: 16/907,777

(22) Filed: Jun. 22, 2020

(65) Prior Publication Data

US 2020/0315921 A1 Oct. 8, 2020

Related U.S. Application Data

(62) Division of application No. 15/439,711, filed on Feb. 22, 2017, now Pat. No. 10,722,432.

(Continued)

(51) Int. Cl.
*A61M 5/31* (2006.01)
*A61J 15/00* (2006.01)
(Continued)

(52) U.S. Cl.
CPC .......... *A61M 5/315* (2013.01); *A61J 15/0076* (2015.05); *A61J 15/0096* (2013.01); *A61M 5/1456* (2013.01); *A61M 5/1458* (2013.01); *A61M 5/31513* (2013.01); *A61M 39/10* (2013.01); *A61M 5/1417* (2013.01); *A61M 2209/086* (2013.01)

(58) Field of Classification Search
CPC ........ A61M 5/3137; A61M 2005/3139; A61M 2005/3142; A61M 5/31511
See application file for complete search history.

(56) References Cited

U.S. PATENT DOCUMENTS 2,051,940 A * 8/1936 Wright .................... A47J 47/18
383/14
3,026,872 A 3/1962 Prater, Jr.
(Continued)

FOREIGN PATENT DOCUMENTS

DE 2108381 A1 8/1972
DE 29617949 U1 4/1997
(Continued)

OTHER PUBLICATIONS

International Search Report & Written Opinion for PCT/US2011/051338; dated Feb. 15, 2012; 20 pgs.

(Continued)

*Primary Examiner* — William R Carpenter
(74) *Attorney, Agent, or Firm* — Dority & Manning, P.A.

(57) ABSTRACT

A plunger for movably mounting within a cavity or barrel of a syringe. The plunger includes a contact face having a flange movably mounted thereto, wherein the flange is movable between an open configuration wherein an opening is formed between the flange and a portion of the plunger, the opening configured for engagement with an IV hook or other engagement member, and a closed configuration wherein the upper surfaces of the contact face and the flange are generally planar with one another.

11 Claims, 14 Drawing Sheets

Related U.S. Application Data

(60) Provisional application No. 62/299,604, filed on Feb. 25, 2016.

(51) Int. Cl.
*A61M 5/145* (2006.01)
*A61M 5/315* (2006.01)
*A61M 39/10* (2006.01)
*A61M 5/14* (2006.01)

(56) References Cited

U.S. PATENT DOCUMENTS

| | | | |
|---|---|---|---|
| 3,113,873 A | | 12/1963 | Krause |
| 3,119,541 A | * | 1/1964 | Lynn .................. B65D 51/242 229/5.5 |
| 3,341,047 A | * | 9/1967 | Nauta .................. B65D 25/32 215/397 |
| 3,581,928 A | | 6/1971 | St. Amand |
| 3,731,684 A | | 5/1973 | Spiegel |
| 3,880,311 A | | 4/1975 | McPhee |
| 3,885,562 A | | 5/1975 | Lampkin |
| 3,900,184 A | | 8/1975 | Burke et al. |
| 3,910,273 A | | 10/1975 | Arlers |
| 4,153,056 A | | 5/1979 | Silver et al. |
| 4,356,824 A | | 11/1982 | Vazquez |
| D267,536 S | | 1/1983 | Findlay |
| 4,392,851 A | | 7/1983 | Elias |
| 4,413,741 A | | 11/1983 | Curchack |
| 4,460,143 A | | 7/1984 | Ohama |
| D282,807 S | | 3/1986 | Hasse |
| D282,962 S | | 3/1986 | Gerber |
| D288,667 S | * | 3/1987 | Miner .................. D9/453 |
| D307,795 S | | 5/1990 | Frantz |
| 4,994,048 A | | 2/1991 | Metzger |
| 5,137,511 A | * | 8/1992 | Reynolds .............. A61M 5/284 604/416 |
| 5,137,527 A | | 8/1992 | Miller et al. |
| D330,862 S | | 11/1992 | Shibley et al. |
| D332,379 S | * | 1/1993 | Murphy .................. D7/391 |
| 5,202,533 A | | 4/1993 | Vandersteen |
| 5,232,112 A | * | 8/1993 | Howard .................. B65D 25/32 220/768 |
| 5,244,113 A | * | 9/1993 | Stymiest ............ B65D 47/0885 215/396 |
| 5,279,566 A | | 1/1994 | Kline, Jr. et al. |
| 5,460,603 A | | 10/1995 | DeSantis |
| 5,549,550 A | | 8/1996 | Mazer et al. |
| 5,611,787 A | | 3/1997 | Demeter et al. |
| 5,746,715 A | | 5/1998 | Mazer et al. |
| 5,746,733 A | | 5/1998 | Capaccio et al. |
| 5,755,689 A | | 5/1998 | Mazer et al. |
| 5,779,668 A | | 7/1998 | Grabenkort |
| 5,832,971 A | | 11/1998 | Yale et al. |
| 5,843,042 A | | 12/1998 | Rem |
| 6,019,747 A | | 2/2000 | McPhee |
| 6,029,946 A | | 2/2000 | Doyle |
| 6,036,669 A | | 3/2000 | Cole et al. |
| 6,065,649 A | | 5/2000 | Scoggins |
| 6,277,092 B1 | | 8/2001 | Cole et al. |
| D447,797 S | | 9/2001 | O'Dell et al. |
| 6,290,206 B1 | | 9/2001 | Doyle |
| D461,243 S | | 8/2002 | Niedospial, Jr. |
| 6,482,170 B1 | | 11/2002 | Andersen |
| 6,541,802 B2 | | 4/2003 | Doyle |
| D474,115 S | * | 5/2003 | Walsh .................. D9/532 |
| 6,752,790 B2 | | 6/2004 | Coombs |
| 6,766,917 B1 | * | 7/2004 | Blewitt, III .......... B65D 51/242 215/399 |
| D511,457 S | * | 11/2005 | Biesecker .................. D9/443 |
| 6,962,563 B2 | | 11/2005 | Yasunaga |
| 7,118,554 B2 | | 10/2006 | Sibbitt |
| D552,773 S | | 10/2007 | Greenberg |
| D578,210 S | | 10/2008 | Muta et al. |
| 7,560,686 B2 | | 7/2009 | Bisch et al. |
| D618,347 S | | 6/2010 | Bradshaw |
| 7,842,217 B2 | | 11/2010 | Enns et al. |
| 7,846,131 B2 | | 12/2010 | Hudson et al. |
| D632,144 S | | 2/2011 | Weisenbach |
| D635,249 S | | 3/2011 | Becker |
| 7,921,847 B2 | | 4/2011 | Totz |
| 7,955,315 B2 | | 6/2011 | Feinberg et al. |
| 7,980,131 B2 | | 7/2011 | Barton |
| D646,531 S | | 10/2011 | Murphy |
| 8,053,721 B2 | | 11/2011 | Bisch et al. |
| D654,584 S | | 2/2012 | Costello et al. |
| D654,585 S | | 2/2012 | Costello et al. |
| 8,162,916 B2 | | 4/2012 | Knight |
| 8,231,597 B2 | | 7/2012 | Knight |
| 8,366,697 B2 | | 2/2013 | Knight |
| 8,540,683 B2 | | 9/2013 | Williams, Jr. et al. |
| 8,550,418 B2 | | 10/2013 | Gesler, III |
| D703,997 S | * | 5/2014 | Munari .................. D7/393 |
| 8,715,244 B2 | | 5/2014 | Prechtel et al. |
| 8,777,900 B2 | | 7/2014 | Hershey et al. |
| D720,218 S | * | 12/2014 | Hutson .................. D9/449 |
| 8,992,488 B2 | | 3/2015 | Ingram et al. |
| D742,064 S | * | 10/2015 | Leidel .................. D27/167 |
| 9,301,587 B2 | | 4/2016 | D'Amico |
| 9,333,288 B2 | | 5/2016 | Hilliard et al. |
| D759,500 S | * | 6/2016 | Bell .................. D9/503 |
| 9,433,562 B2 | | 9/2016 | Ingram et al. |
| 9,433,729 B2 | | 9/2016 | Ingram et al. |
| D853,182 S | * | 7/2019 | Adams, Jr. .................. D7/392.1 |
| 2003/0014005 A1 | | 1/2003 | Chiba et al. |
| 2004/0054350 A1 | | 3/2004 | Shaughnessy et al. |
| 2006/0264824 A1 | * | 11/2006 | Swisher, III ........ A61M 5/3129 604/110 |
| 2007/0060898 A1 | | 3/2007 | Shaughnessy et al. |
| 2007/0123822 A1 | | 5/2007 | Wang et al. |
| 2007/0265579 A1 | | 11/2007 | Kleyman et al. |
| 2008/0097348 A1 | | 4/2008 | Itrich |
| 2008/0183153 A1 | | 7/2008 | Enns |
| 2008/0255501 A1 | | 10/2008 | Hogendijk et al. |
| 2008/0255523 A1 | | 10/2008 | Grinberg |
| 2009/0287161 A1 | | 11/2009 | Traub et al. |
| 2010/0249719 A1 | | 9/2010 | Fojtik |
| 2011/0046568 A1 | | 2/2011 | Enns et al. |
| 2011/0184383 A1 | * | 7/2011 | Hasegawa ........... A61M 5/1456 604/151 |
| 2011/0192489 A1 | | 8/2011 | Pobitschka |
| 2011/0270227 A1 | | 11/2011 | Klechner et al. |
| 2012/0071853 A1 | * | 3/2012 | Ingram ............... A61M 5/1452 604/218 |
| 2012/0150111 A1 | | 6/2012 | Hershey et al. |
| 2013/0082057 A1 | | 4/2013 | Schiff et al. |
| 2013/0131606 A1 | | 5/2013 | Bertocci |
| 2014/0039462 A1 | | 2/2014 | Ingram et al. |
| 2014/0213985 A1 | | 7/2014 | Teucher et al. |
| 2015/0148753 A1 | | 5/2015 | Ingram et al. |
| 2016/0287798 A1 | | 10/2016 | Holmqvist |

FOREIGN PATENT DOCUMENTS

| | | |
|---|---|---|
| EP | 0 481 250 A1 | 9/1991 |
| EP | 1 110 568 A2 | 6/2001 |
| EP | 1 980 282 A1 | 10/2008 |
| FR | 1126718 | 6/1955 |
| JP | 2015192729 A * | 11/2015 |
| WO | WO 2007/095541 A2 | 8/2007 |
| WO | WO 2009/141510 A1 | 11/2009 |
| WO | WO 2011/026156 A1 | 3/2011 |
| WO | WO 2012/037082 A1 | 3/2012 |

OTHER PUBLICATIONS

International Search Report & Written Opinion for PCT/US2012/60987; dated Jan. 25, 2013; 13 pgs.

International Search Report & Written Opinion for PCT/US2013/53631; dated Oct. 11, 2013; 10 pgs.

International Search Report & Written Opinion for PCT/US2017/018957; dated May 15, 2017; 10 pgs.

(56) References Cited

OTHER PUBLICATIONS

NeoMed Enteral Syringe; 2007; 1 pg.

* cited by examiner

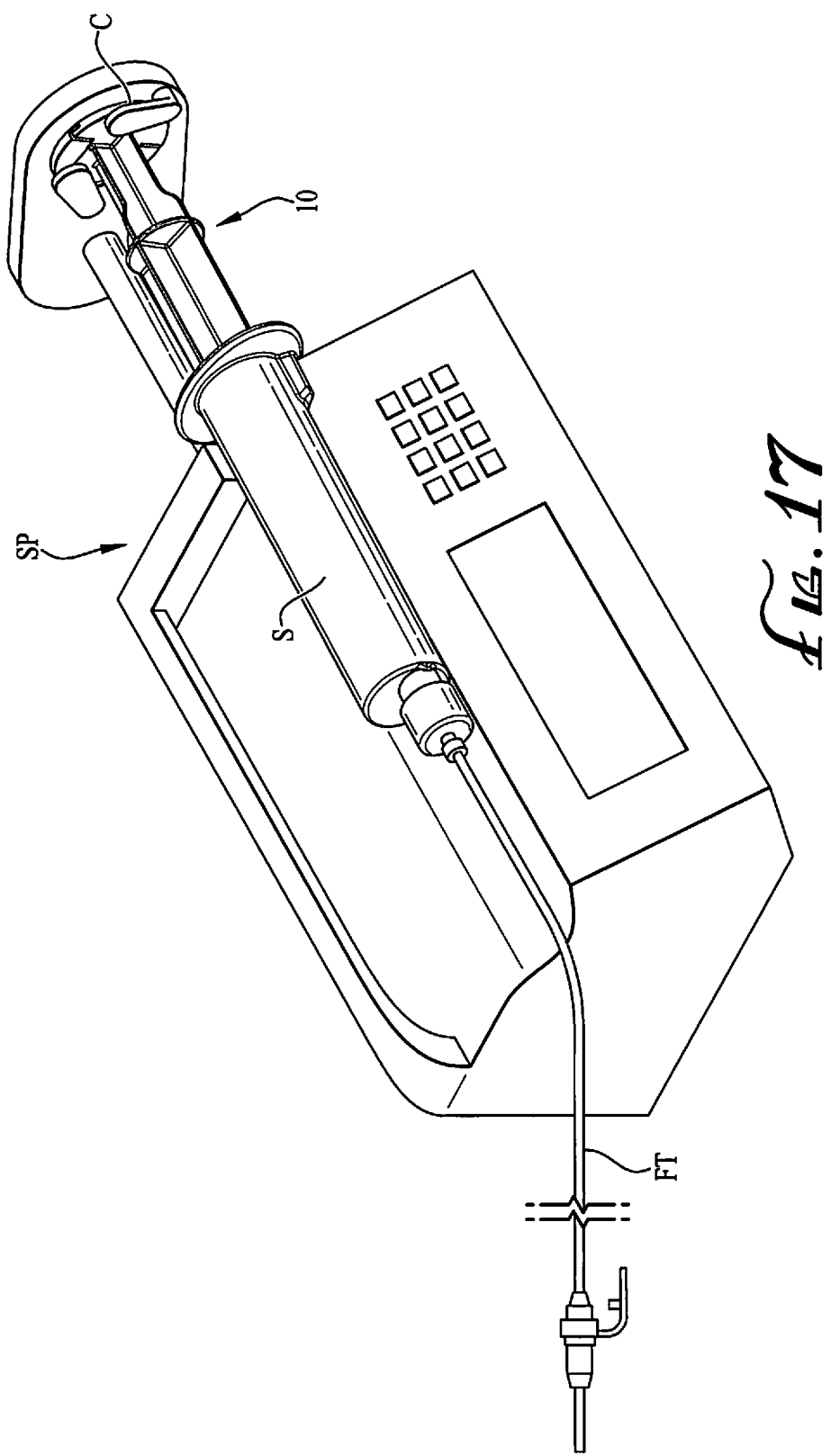

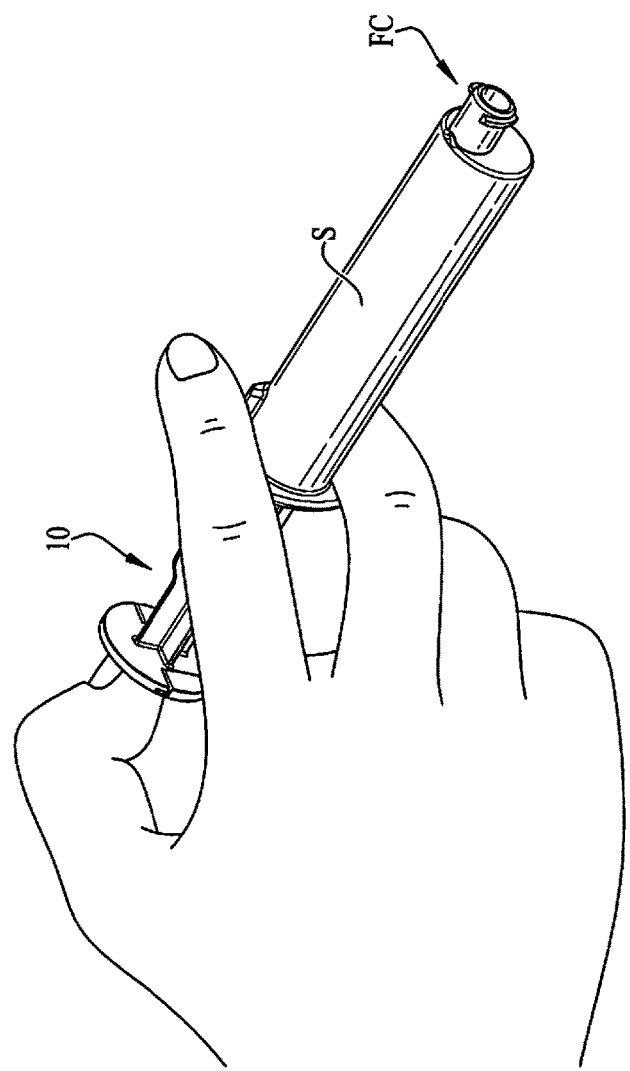
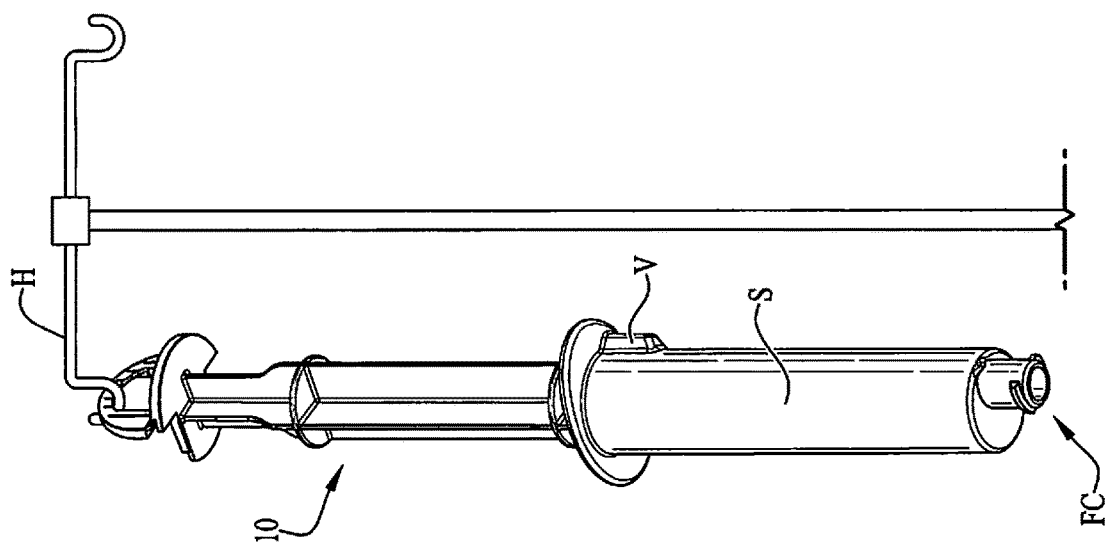

SYRINGE PLUNGER WITH HINGED FLANGE

CROSS-REFERENCE TO RELATED APPLICATION

The present application is a divisional of U.S. application Ser. No. 15/439,711, filed on Feb. 22, 2017, granted as U.S. Pat. No. 10,722,432 on Jul. 28, 2020, which claims the priority benefit of U.S. Provisional Patent Application Ser. No. 62/299,604 filed Feb. 25, 2016, the entirety of which are hereby incorporated by reference herein.

TECHNICAL FIELD

The present invention relates generally to the field of collection and dispensing of fluids, and more particularly to a syringe plunger having a hinged flange for application of pressure on the plunger and for hanging the plunger.

BACKGROUND

Syringe pumps, or drivers, are small infusion pumps used to gradually administer fluids from a syringe to a patient. When administering drugs (e.g. painkillers, antiemetics, etc.) syringe pumps prevent periods during which the medication levels in the blood are too high or too low, and prevent a patient from having to repeatedly take tablets or pills. Additionally, syringe pumps are effective at administering medication over many minutes or hours and often reduce errors by caretakers. One particular use of syringe pumps is in the field of enteral feeding administration. For example, syringe pumps are especially useful for the administration of breast milk (or suitable substitutes), formula, medication, nutritional supplements or other enteral fluids in the care and treatment of neonatal children.

Syringes can also be used with gravity feed systems, for example, when administering nutrients and/or medications to a neonatal patient. When administering fluids to a patient via a gravity-feed system, the syringe plunger can be removed from the syringe body to prevent a vacuum from developing inside the syringe as the fluid leaves the syringe and enters the patient. The removal of the plunger from the syringe body is often seen as a drawback to this process and requires that a user take special care in storing the plunger while the syringe is being utilized. In the past, users have strapped the plunger to the syringe body or otherwise stored the plunger on a sterile tray or other location to avoid permanently separating these components. Removing the plunger from the syringe body can expose the contents of the syringe to unwanted pathogens, dust or other foreign matter, which can be harmful to a patient.

To alleviate the need for removing the plunger from the syringe to allow for venting, syringes have been developed to provide venting while at least a portion of the plunger is still engaged with the syringe, for example, so that the drawbacks of potentially exposing the plunger to unwanted pathogens, dust or foreign matter is eliminated. U.S. Published patent application Ser. No. 13/231,185, Patent Application Publication No. US 2012/0071853 and U.S. Published patent application Ser. No. 14/614,156, Patent Application Publication No. US 2015/0148753, show vented syringes for use with gravity feed systems, which are hereby incorporated herein by reference for all purposes.

When administering fluids to a patient via a gravity feed system, it is generally desirable to hang the syringe and plunger assembly at a position above the patient that is receiving the fluids from the syringe. Some syringes may include a handle mounted to the syringe body for permitting hanging. Alternatively, a hole or tether can be provided on a flange of a syringe plunger for hanging the syringe. U.S. Published patent application Ser. No. 14/224,297, Patent Application Publication No. US 2014/0207098, shows a vented syringe plunger including a tether provided thereon, which is hereby incorporated herein by reference for all purposes.

In some instances, modifications made to a syringe to allow for hanging for use with gravity feed applications can negatively affect compatibility of the syringe with metering pumps. Thus, it can be seen that needs exist for improved syringes having a plunger that can be utilized for hanging in gravity-feed applications, and that is compatible with metering pumps in applications.

It is to the provision of a syringe having a hinged plunger flange meeting these and other needs that the present invention is primarily directed.

SUMMARY

The present invention relates to a syringe having a hinged plunger flange, which allows the syringe to be compatible for use with a metering pump when the hinged plunger flange is in a down, pump compatible position and for use in hanging the syringe when the hinged plunger flange is in a second position, for example, an upright or expanded configuration.

In one aspect, the invention relates to a syringe having a plunger for movably mounting within a syringe cavity, the plunger including a first end and a second end, and a middle body portion extending between the first and second ends, wherein a sealing head is provided at the first and a contact face is provided at the second end, wherein the contact face comprises a fixed portion and a flange portion movable relative to the fixed portion between an open configuration and a closed configuration, wherein in the open configuration an IV hook or other engagement member can engage an opening formed in the flange portion.

In another aspect, the invention relates to a syringe plunger for movably mounting within a syringe barrel. The plunger includes a first end and a second end, and a middle body portion extending between the first and second ends. In example embodiments, a sealing head is provided at the first end and a contact face is provided at the second end, wherein the contact face includes a fixed portion mounted to the middle body portion and a flange portion mounted to the fixed portion and movable relative to the fixed portion between an open configuration and a closed configuration. In example embodiments, in the open configuration an IV hook or other engagement member can engage an opening formed in the flange portion.

In another aspect, the invention relates to a syringe plunger for movably mounting within a syringe barrel. The syringe plunger includes a contact face including a hinged portion and a fixed portion, wherein the hinged portion is pivotally coupled to the fixed portion and movable between an open configuration and a closed configuration, wherein in the open configuration an opening is accessible for receiving a hanging support member In yet another aspect, the invention relates to a syringe including a syringe barrel and a syringe plunger adapted to advance and retract within the syringe barrel. The syringe plunger includes a contact flange with a hinged portion movable between a retracted position adapted for use with a syringe pump or manual actuation, and an extended position adapted for hanging from a support.

These and other aspects, features and advantages of example embodiments of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 17 shows a syringe comprising the plunger of FIG. 1 movably mounted therein, and showing the syringe and plunger being engaged with a syringe pump according to an example embodiment of the present invention.

FIG. 18 shows a syringe comprising the plunger of FIG. 2, and showing the flange thereof in an extended or upright configuration whereby a hook or other support engages the flange to suspend the syringe for use as a gravity feed system.

FIG. 19 shows a syringe comprising the plunger of FIG. 1, and showing a user manually operating the plunger by depressing the pressure plate with the hinged flange in a flat or collapsed configuration.

DETAILED DESCRIPTION OF EXAMPLE EMBODIMENTS

Figure 1:
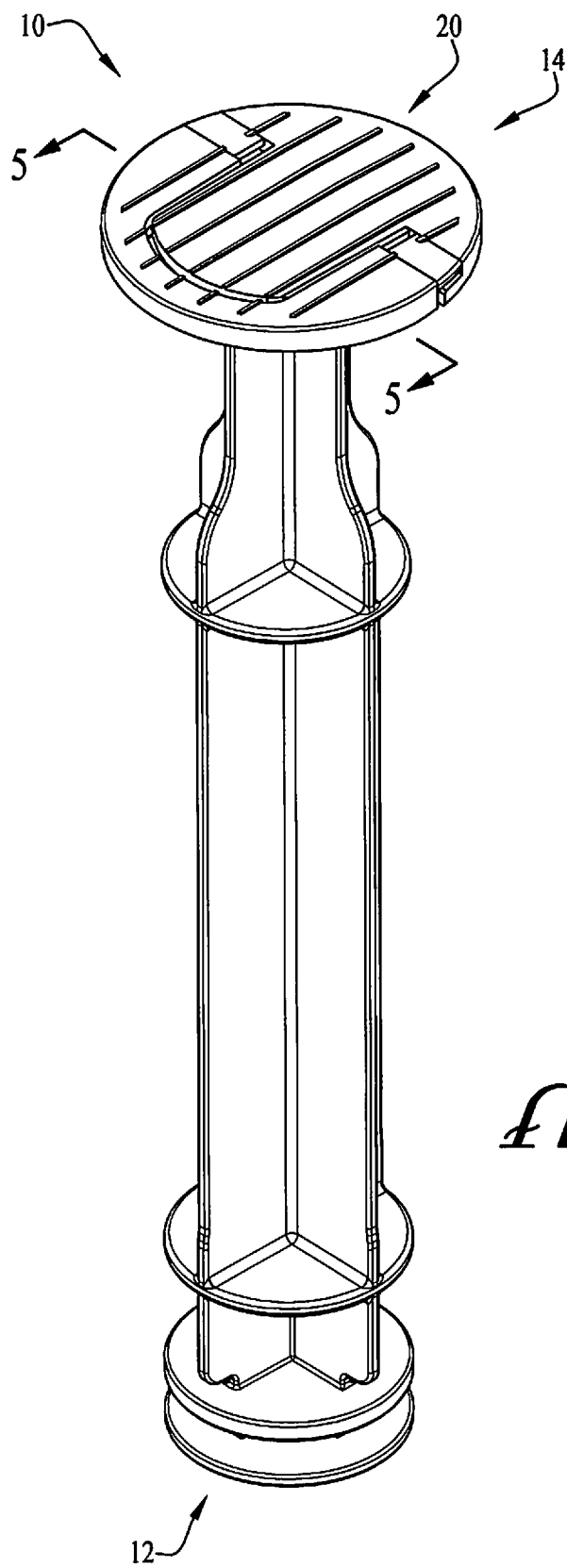
FIG. 1 is a perspective view of a syringe plunger having a pivoting or hinged pressure flange according to an example embodiment of the present invention, the flange being positioned in a flat or collapsed configuration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-8 show a syringe plunger 10 according to an example embodiment of the present invention. In example forms, the plunger 10 is configured for sealingly engaging the interior containment cavity of a syringe barrel or body, for example, wherein advancement or retraction of the plunger 10 within the cavity of the syringe barrel varies the contained volume of the syringe to discharge or fill the syringe with fluid contents such as fluids for enteral delivery.

According to example forms, the syringe is optionally a vented syringe, having one or more vents allowing fluid passage between the syringe barrel and plunger, such that the plunger is movable between a vented position and a sealed/vacuum position. U.S. Published patent application Ser. No. 13/231,185, Patent Application Publication No. US 2012/0071853; U.S. Published patent application Ser. No. 14/224,297, Patent Application Publication No. US 2014/0207098; and U.S. Published patent application Ser. No. 14/614,156, Patent Application Publication No. US 2015/0148753, are hereby incorporated herein by reference, and show example vented syringes for use with gravity feed systems, the vented syringe barrels of which may be adapted to receive a syringe plunger having a hinged pressure flange according to example embodiments of the present invention.

Figure 2:
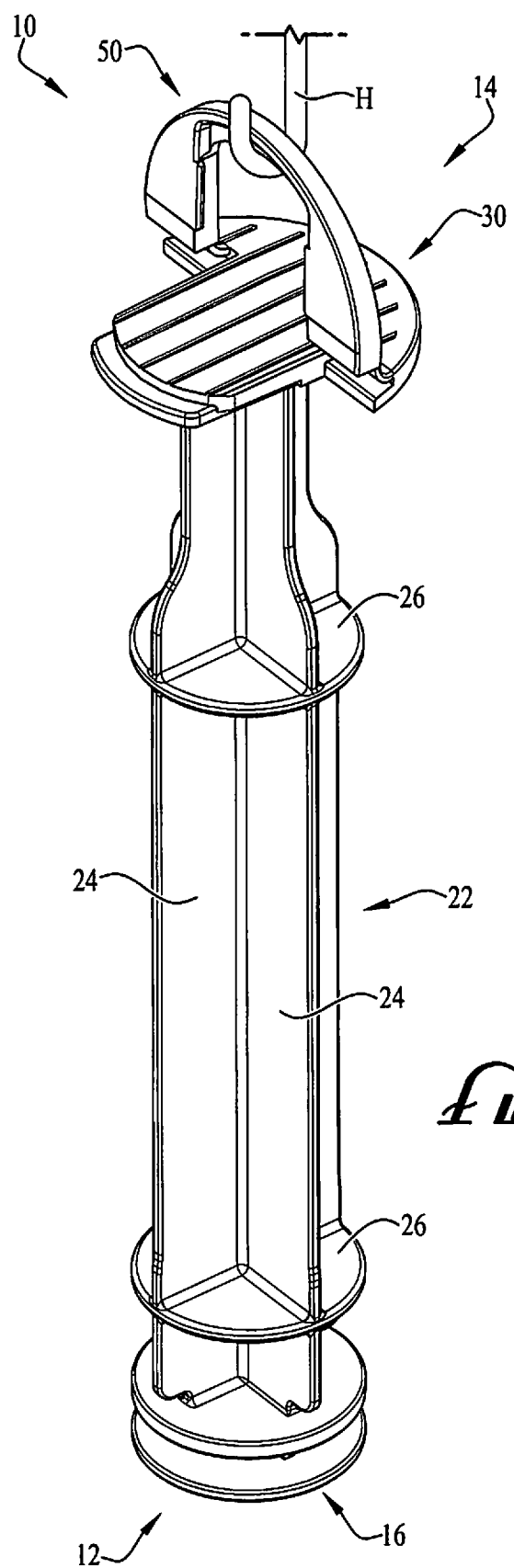
FIG. 2 shows the plunger of FIG. 1, showing the flange positioned in an extended or upright configuration and showing a hook portion being looped through a portion of the flange for hanging the plunger (and syringe).
Figure 3:
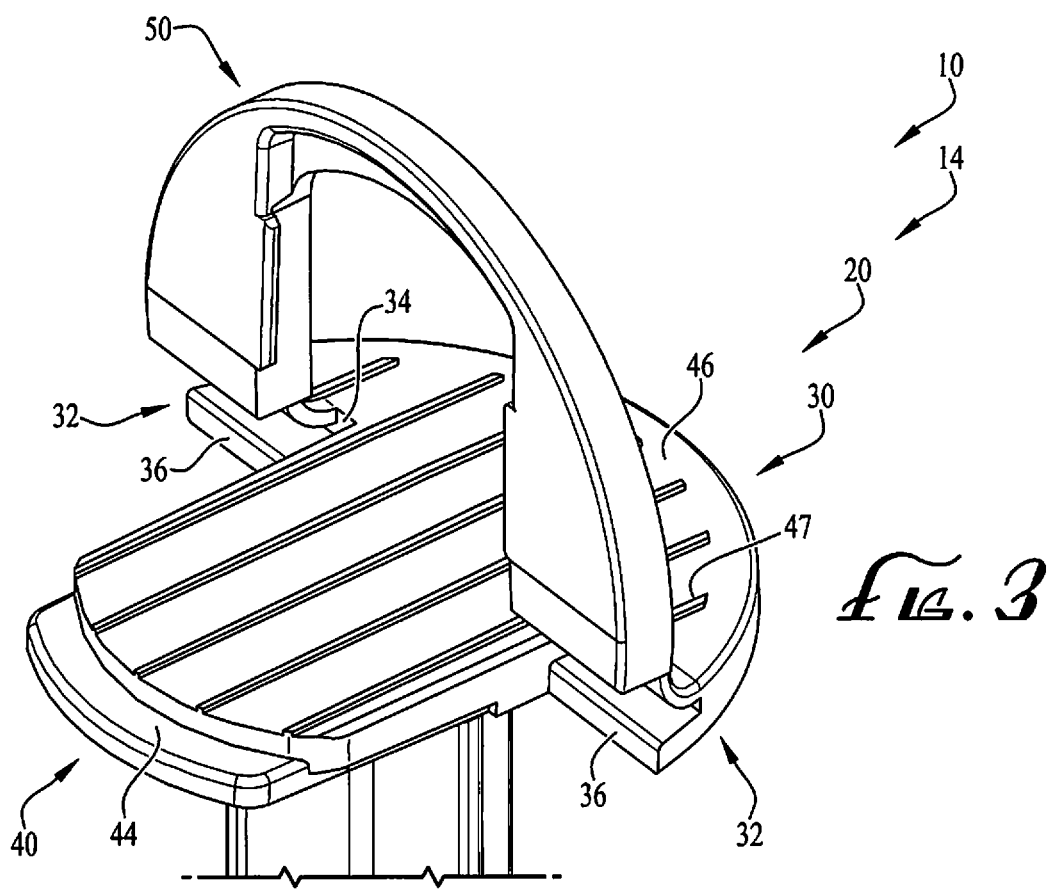
FIG. 3 shows a detailed view of a portion of the plunger of FIG. 2.

In example embodiments, the syringe plunger 10 comprises a first or distal end 12 and a second or proximal end 14. The distal end 12 comprises a sealing head 16 for tightly engaging an inner wall of a cavity of a syringe body with a fluid tight seal, and the proximal end 14 comprises a pressure plate, thumb pad or contact face 20 to engage a depressor of a syringe pump (or permit user manipulation by hand operation). A main body portion 22 of the plunger 10 generally connects the first end 12 to the second end 14. In example forms, the main body portion 22 generally comprises one or more planar ribs 24 connecting the sealing head 16 to the contact face 20. In one form, the main body portion 22 comprises generally uniform ribs 24 having a cruciform cross-section in the shape of a plus (+) sign. Optionally, cross-sections of other desired shapes and configurations can be chosen as desired. As shown in FIG. 2 and according to example embodiments, the contact face 20 of the syringe plunger 10 comprises a fixed portion 30 and a hinged or flange portion 50 generally mounted to move relative to the fixed portion 30. As depicted in FIG. 1, the ribs 24 can comprise one or more cutouts, which reduce the overall diameter of the ribs to a size for engagement with the fixed portion 30 of the contact face 20. Furthermore, one or more discs or supports 26 can be formed with one or more of the ribs 24 along the length of the main body portion 22 for providing additional support.

As depicted in FIGS. 1-4, the flange portion 50 of the contact face 20 of the syringe plunger 10 is generally hinged to pivot relative to two generally symmetrical wings or arms 32 extending from opposite sides of the fixed portion 30. According to one example form, the contact face 20 of the plunger 10 is generally disc-shaped or generally circular whereby the fixed portion 30 is generally T-shaped and the flange portion 50 is generally U-shaped, for example, wherein the ends of the U-shaped flange portion 50 are pivotally or hingedly mounted to upper horizontal ends 34 of the T-shaped fixed portion 30 (e.g., the arms 32), such that in a retracted or collapsed configuration (see FIG. 1) a central member or portion 40 of the T-shaped fixed portion 30 can be received in an 56 opening of the U-shaped flange portion 50 to form a generally flat and uniform contact face 20 adapted for manipulation by a user or a syringe pump.

In example embodiments, a living hinge 60 is provided between the fixed and flange portions 30, 50 of the syringe plunger 10 such that the two portions are generally integrally formed together with a thin web of flexible material extending therebetween, allowing for hinged movement of the flange portion 50 relative to the fixed portion 30, for example, between a closed, flat, collapsed or retracted position (see FIG. 1), and an open, expanded, extended or upright configuration (see FIGS. 2-4) for allowing a hook (e.g., IV hook) or other engagement member to extend through an opening formed in the flange portion for hanging the syringe and plunger in a substantially vertical orientation, for example, wherein the plunger is moved to a vented position to permit discharge of the fluid therein within a feeding tube and to the patient (see FIG. 18). For example, according to example embodiments, the living hinge 60 is generally integrally connected between the upper horizontal ends 34 of the fixed portion 30 (see FIG. 3) and hinge connection faces 62 defined at the ends of the arms 52 of the flange portion 50 (see FIG. 4). Optionally, the living hinge 60 can be provided on other portions of the fixed and flange portions 30, 50, for example, to permit movement of the flange portion 50 relative to the fixed portion 30 between the collapsed configuration (see FIGS. 5 and 8) and the upright configuration.

Figure 4:
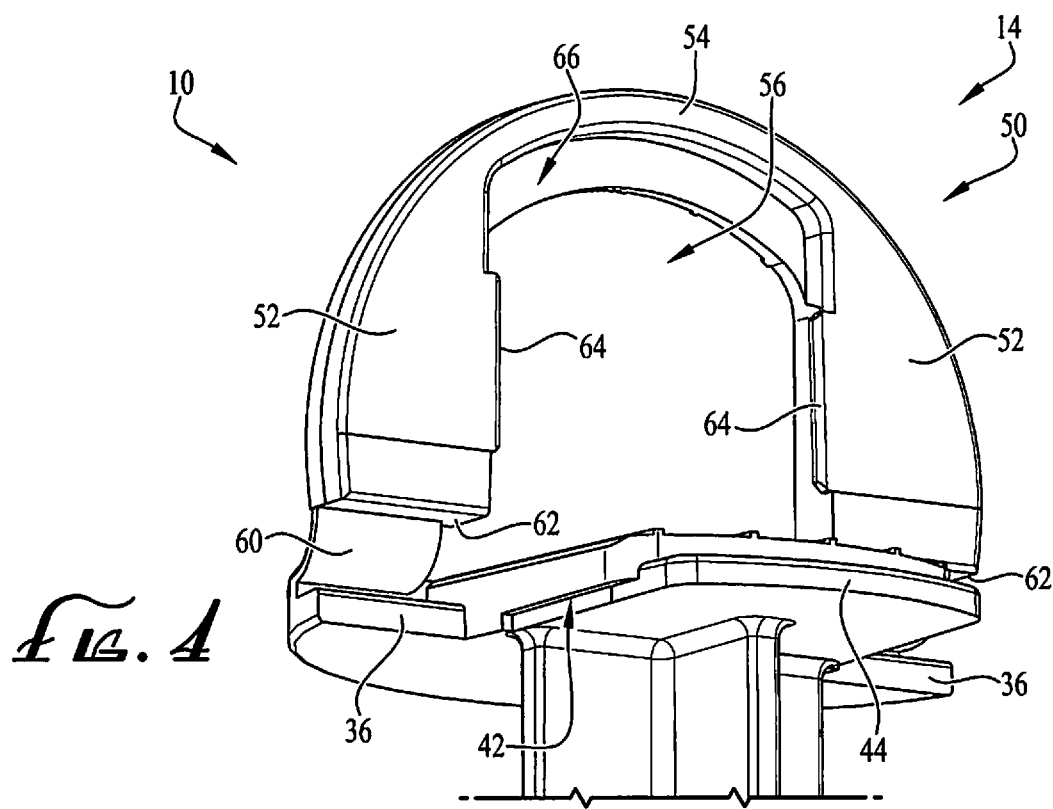
FIG. 4 shows a detailed bottom perspective view of a portion of the plunger of FIG. 3.
Figure 5:
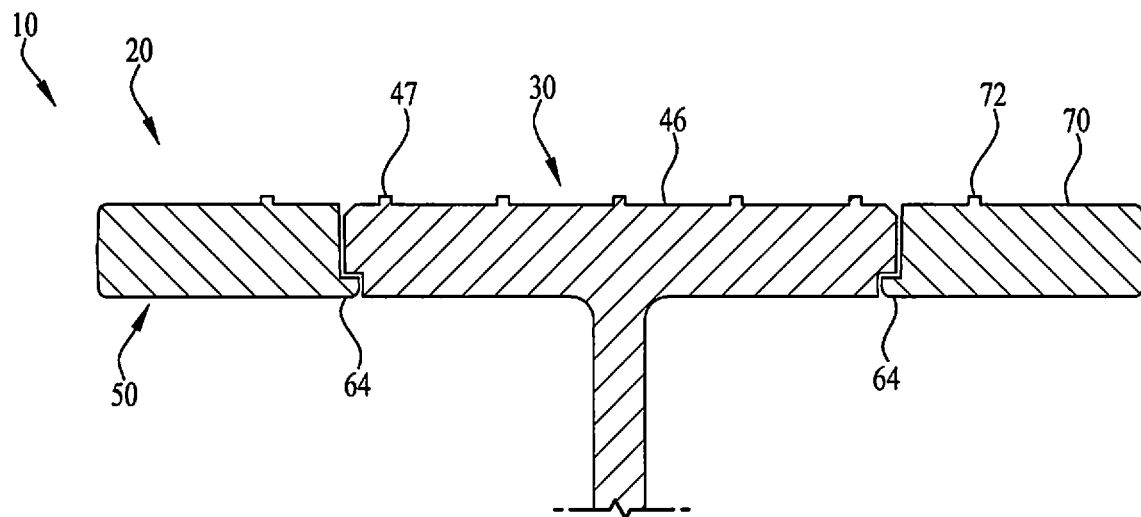
FIG. 5 shows a cross-sectional view of a portion of the plunger of FIG. 1 taken along line 5-5, showing interengagement of portions of the flange with an end plate of the plunger.

According to example embodiments, the flange portion 50 comprises two end extensions or arms 52 that are generally offset from one another and a middle section or central connection portion 54 connecting together top portions of the two arms 52, for example, to form a generally upside-down U-shaped member. In example forms, the contact face or pressure plate 20 is generally circular in shape, and thus, the middle section 54 and outer portions of the arms 52 are generally arcuate or radiused to match the profile of the contact face. As depicted in FIGS. 4-5, the flange portion 50 comprises at least one engagement or coupling feature for providing coupling engagement with a portion of the fixed member, for example, when the flexible member is moved to the collapsed configuration such that upper surfaces 46, 70 of the fixed and flange portions 30, 50 are substantially planar relative to each other. In example embodiments, a ridge, protrusion, clip or ledge 64 is provided along interior portions of the arms 52 for providing removable engagement with portions of the fixed portion.

In example embodiments, opposite sides of the central member 40 of the fixed portion 30 comprise channels 42 for receiving and providing coupling interengagement with the ledges 64 of the arms 52 of the flange portion 50. Generally, the features of the upper surfaces of the fixed and flange portions are matching such that in the retracted configuration the contact face is completed and can be used normally (e.g., for compressing in a pump or grasping for moving the plunger relative to the syringe barrel). In example embodiments, the upper surfaces of the fixed and flange portions 30, 50 comprise gripping or surface features in the form of a linear array of ribs or channels. For example, the fixed portion 30 comprises one or more surface features 47 and the flange portion comprises surface features 72. Optionally, other surface features can be provided as desired.

Figure 6:
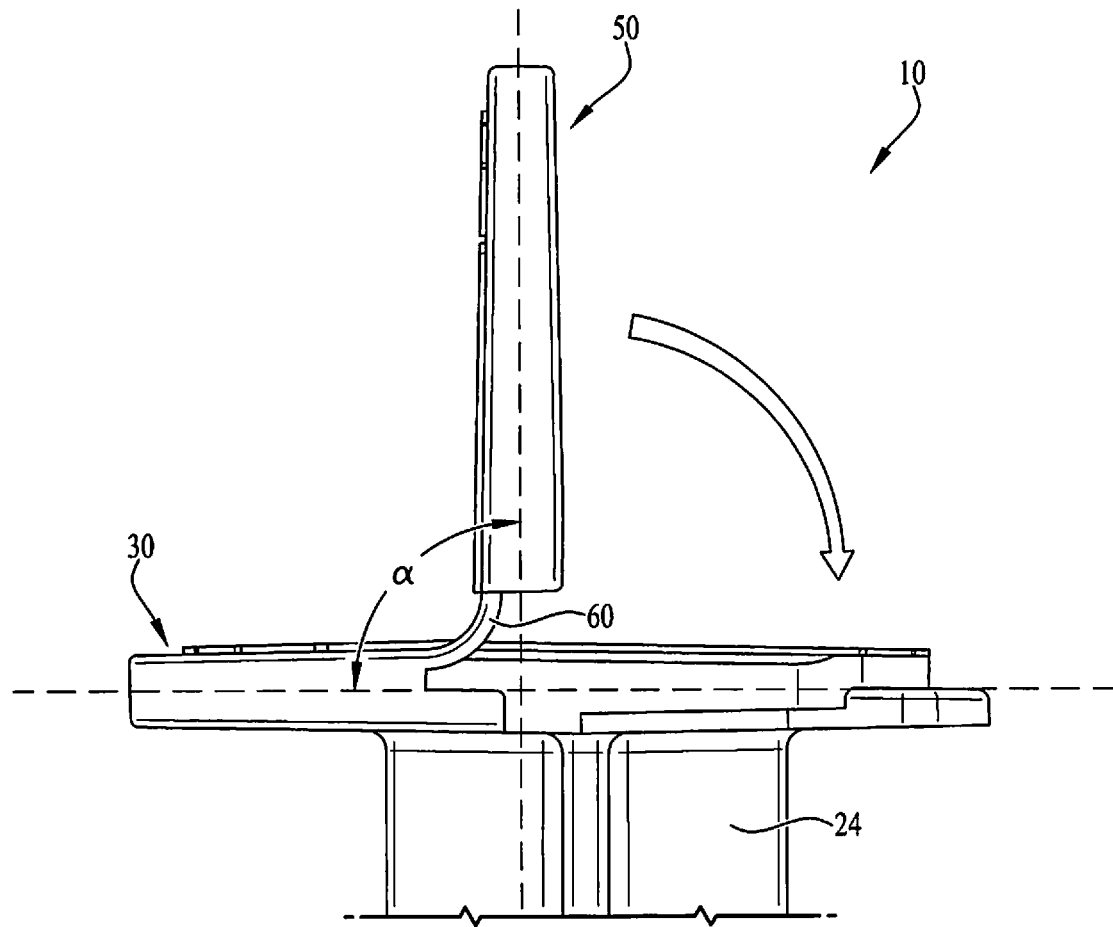
FIG. 6 shows a side view of the plunger of FIGS. 3-4, showing the flange positioned in the extended or upright configuration.
Figure 7:
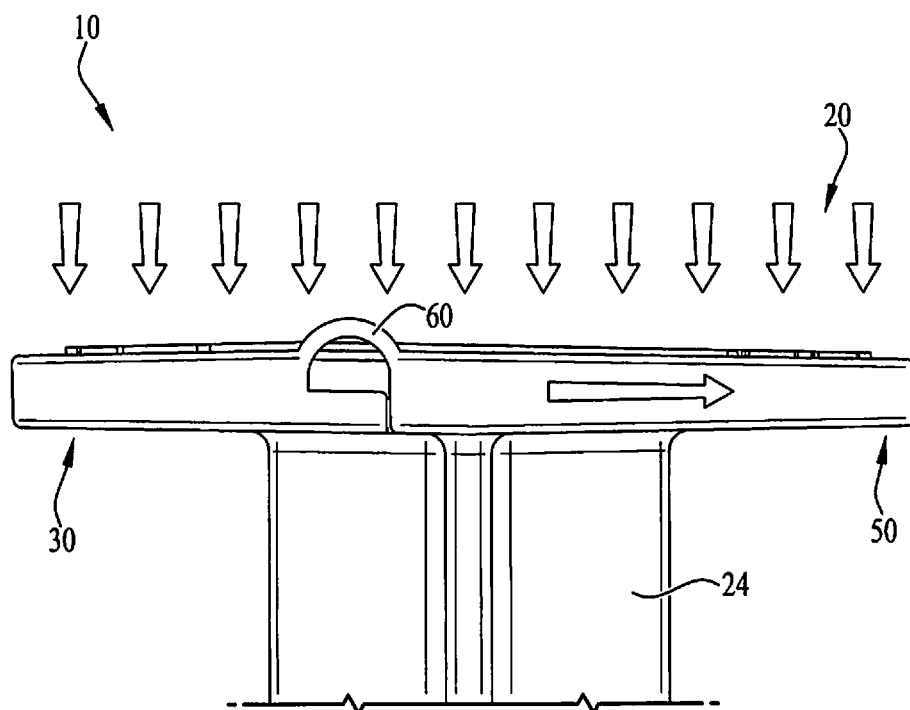
FIG. 7 shows a side view of the plunger with the flange positioned in a substantially flat or collapsed configuration, showing a hinge thereof being at least partially flexed.
Figure 8:
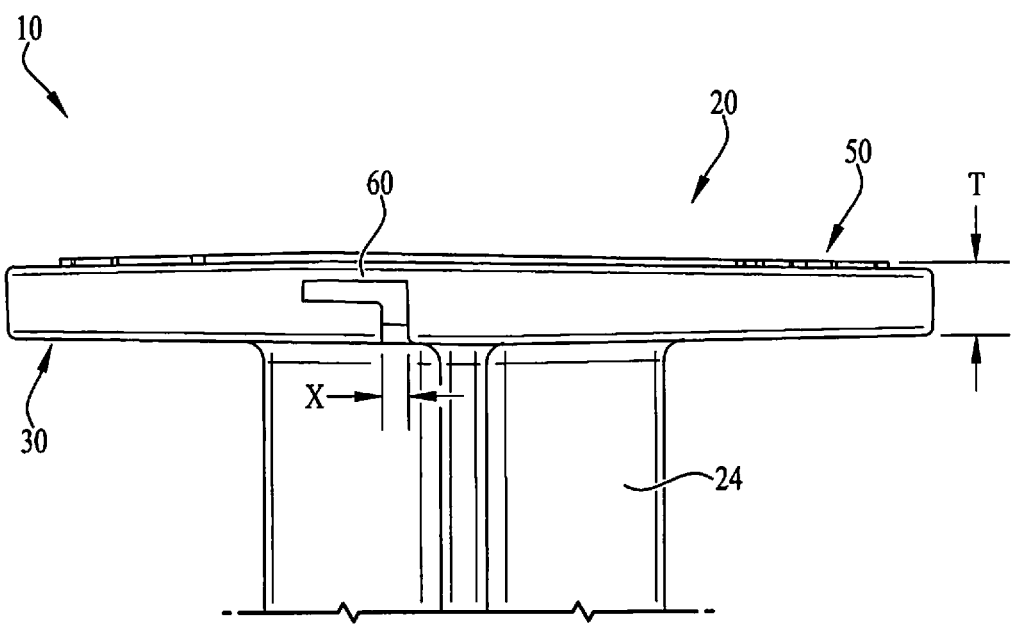
FIG. 8 shows a side view of the plunger of FIG. 1, showing the flange being positioned in a substantially flat or collapsed configuration wherein the hinge connecting the flange to the plunger is substantially unflexed and planar.

In example embodiments, as shown in FIGS. 6-8, moving the flange portion to a retracted or closed position causes the flange portion 50 to become engaged with the fixed portion 30 such that the flange portion 50 is mounted at a position relative to the fixed portion to cause upward bulging or outwardly bowing of the living hinges 60 for example, such that the flange portion is generally positioned at least partially closer than the extension of the flange portion (see FIG. 7). As shown in FIGS. 7-8, a user or feed pump may apply a force to the contact face 20 to move the flange portion 50 outwardly relative to the fixed portion 30. In example embodiments, ends 36 of the arms 32 of the fixed portion 30 relative to ends of the arms 62 of the flange portion 50 comprises a length X of between about 0.1 to about 1 millimeters, more preferably between about 0.2 to about 0.8 millimeters, for example about 0.6 millimeters according to example embodiments. As desired, a user can move the flange portion from a closed position to an open position by pushing upwards on at least a portion of the flange portion while holding the fixed portion and/or the main body portion of the syringe plunger. In example embodiments, the contact face 20 comprises a thickness T of between about 1.50-2.50 millimeters, for example between about 2.00-2.25 millimeters according to an example embodiment of the present invention. Optionally, other thicknesses T can be provided as desired.

Referring back to FIG. 6, the flange portion 50 is in the upright configuration with flange portion 50 generally extending at an angle α relative to the fixed portion 30, for example, wherein α is generally between about 25-165 degrees, more particularly for example between about 45-135 degrees, for example about 90 degrees according to example embodiments. In example embodiments, the plunger 10 is formed by injection molding whereby the flange portion 50 is molded in the upright configuration with the angle α being about 90 degrees. Thus, in a relaxed or equilibrium state, the flange portion 50 generally extends at an angle of about 90 degrees relative to an upper surface of the fixed portion. As such, when the plunger is engaged with a syringe and with the flange portion in the upright configuration, an IV hook or other hook or engagement member can easily engage the flange portion by extending a portion thereof through an opening 56 formed between the arms 52 and the central connection portion 54 of the flange portion 50, and the upper surface 46 of the fixed portion 30 (see FIG. 18).

Figure 9:
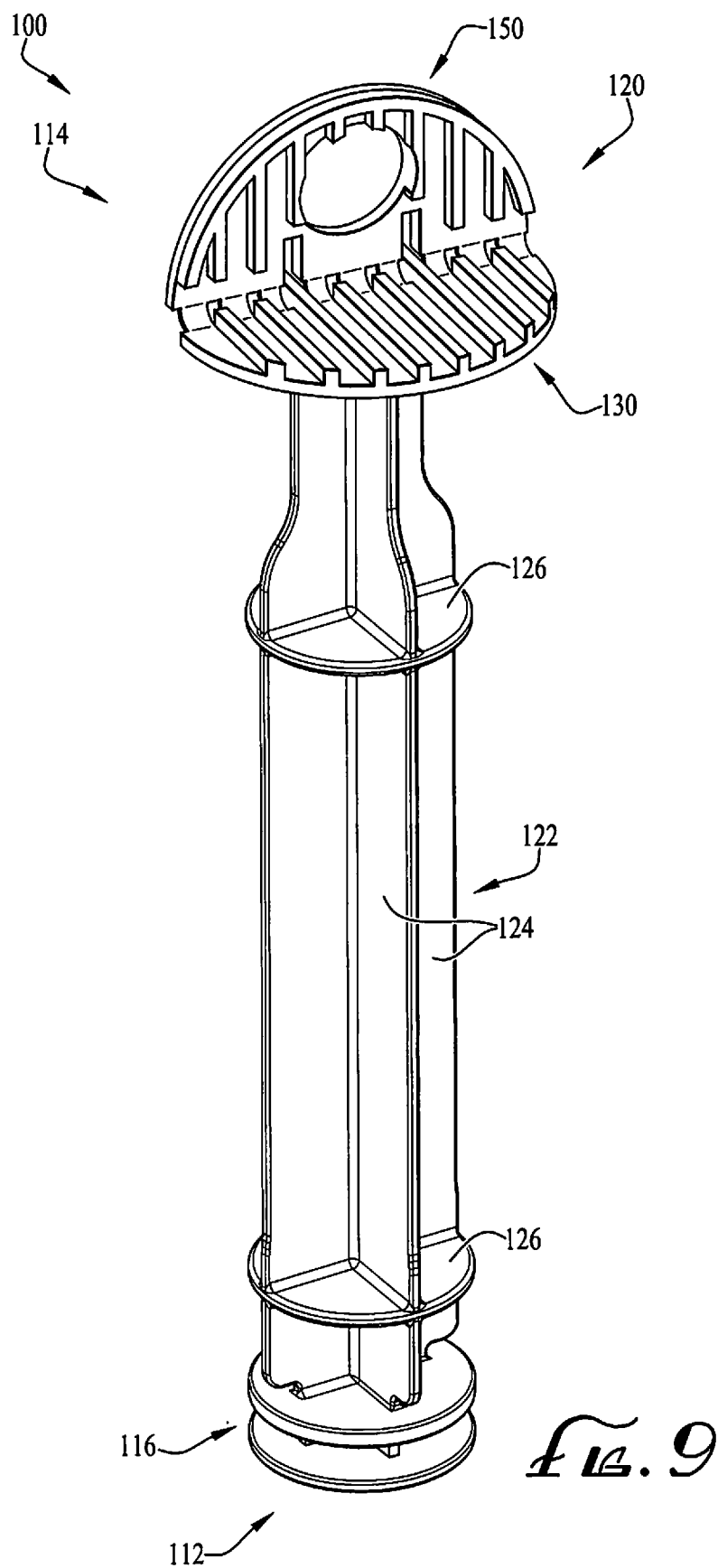
FIG. 9 shows a front perspective view of a syringe plunger having a pivoting or hinged pressure flange according to another example embodiment of the present invention, the flange being positioned in an extended or upright configuration.
Figure 10:
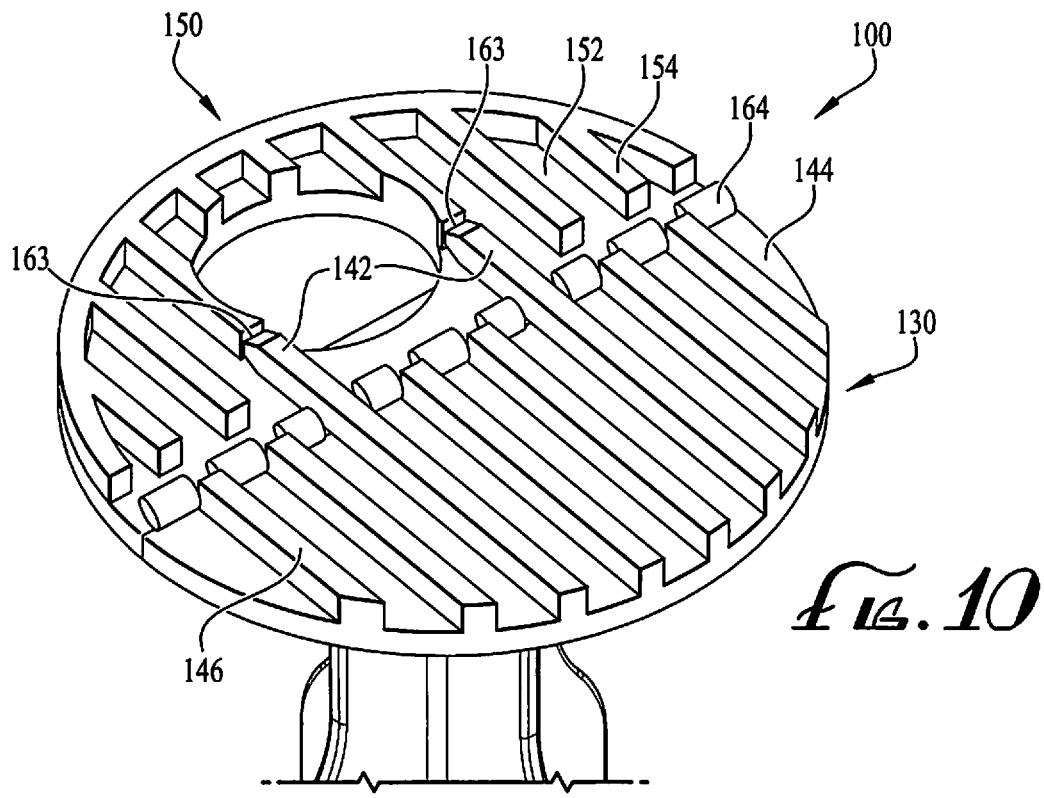
FIG. 10 shows a rear perspective view of the syringe plunger of FIG. 9, the flange being in a flat or collapsed configuration.
Figure 11:
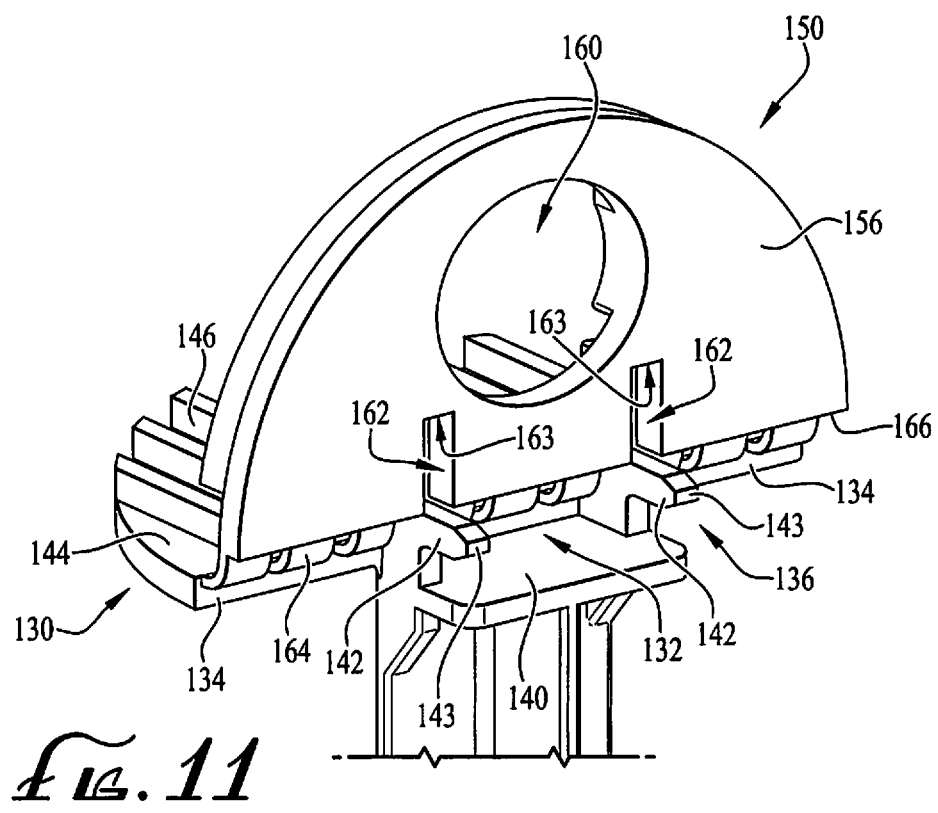
FIG. 11 shows a rear perspective view of a portion of the syringe plunger of FIG. 9.

FIGS. 9-11 show a plunger 100 according to another example embodiment of the present invention. As depicted, the plunger 100 is generally similar to the plunger 10 and comprises a first or distal end 112 and a second or proximal end 114. The distal end 112 comprises a sealing head 116 for tightly engaging an inner wall of a cavity of a syringe body with a fluid tight seal, and the proximal end 114 comprises a pressure plate, thumb pad or contact face 120 to engage a depressor of a syringe pump (or permit user manipulation by hand operation). A main body portion 122 of the plunger 100 generally connects the first end 112 to the second end 114. In example forms, the main body portion 122 generally comprises one or more planar ribs 124 connecting the sealing head 116 to the contact face 120.

In example embodiments, the contact face 120 at the second end 114 comprises a fixed portion 130 and a hinged hanging flange portion 150 that is movable relative to the fixed portion 130. According to example forms, the flange portion 150 is connected to the fixed portion 130 by a plurality resiliently flexible living hinges 164, for example, about 9 separate hinges. Optionally, more or less hinges can be provided as desired. In example embodiments, the fixed portion 130 generally comprises a portion of a complete disc-shaped contact face, and the flange portion 150 comprises the other portion of the complete disc-shaped contact face, and wherein the flexible living hinges 164 generally extend between an end face 134 of the fixed portion 130 and an end face 166 of the flange portion 150, for example, such that the flange portion 150 is movable between the collapsed configuration (FIG. 10) and the upright configuration (FIGS. 9 and 11).

As shown in FIG. 11, the fixed portion 130 comprises at least one interengagement feature 136 for coupling the flange portion 150 in the collapsed configuration, for example, such that the pressure plate 120 can be compatible for engagement with a syringe pump or for being pressed by a user's thumb (see FIGS. 17-19). In example embodiments, the interengagement feature 136 comprises a platform 140 having a pair of engagement fingers 142 extending outwardly from the end face 134 of the fixed portion 130 (and the fingers 142 being generally laterally offset from the platform 140) for being received within a pair of spaced-apart channels or receivers 162 formed in the flange portion 150. In example embodiments, the receivers 162 comprise end engagement surfaces 163 for providing engagement with the fingers 142. For example, in example embodiments, the fingers 142 comprise end surfaces 143 for engaging the end engagement surfaces 163 of the receivers 162 when the flange portion 150 is in the collapsed configuration. Furthermore, when the flange portion 150 is in the collapsed configuration and the end surfaces 143 of the fingers 142 are engaging the end engagement surfaces 163 of the flange portion 150, a lower surface 156 of the flange portion 150 generally contacts the platform 140. In example embodiments, the upper surfaces 144, 152 of the fixed and flange portions 130, 150 comprise surface features 146, 154 in the form of protruding and spaced-apart ribs. In example embodiments, the fingers 142 extending from the fixed portion 130 are generally extensions of two of the surface features 146. According to example embodiments, the fingers 142 generally extend a length such that there is at least some interference of the end surfaces 143 and the end engagement surfaces 163. Optionally, other engagement or coupling features can be provided for coupling the flange portion 130 in the collapsed configuration.

In example embodiments, flange portion 130 can comprise one or more holes, slots or other openings 160 formed therein for receiving an IV hook or other engagement member for suspending the plunger and an attached syringe. In the depicted embodiment shown in FIG. 11, the flange portion 150 generally comprises a circular opening formed through the flange portion 150, for example, about at a midpoint defined therebetweeen. Alternatively, the opening 160 can be other shapes including polygonal, oval, or other shapes as desired.

Figure 12:
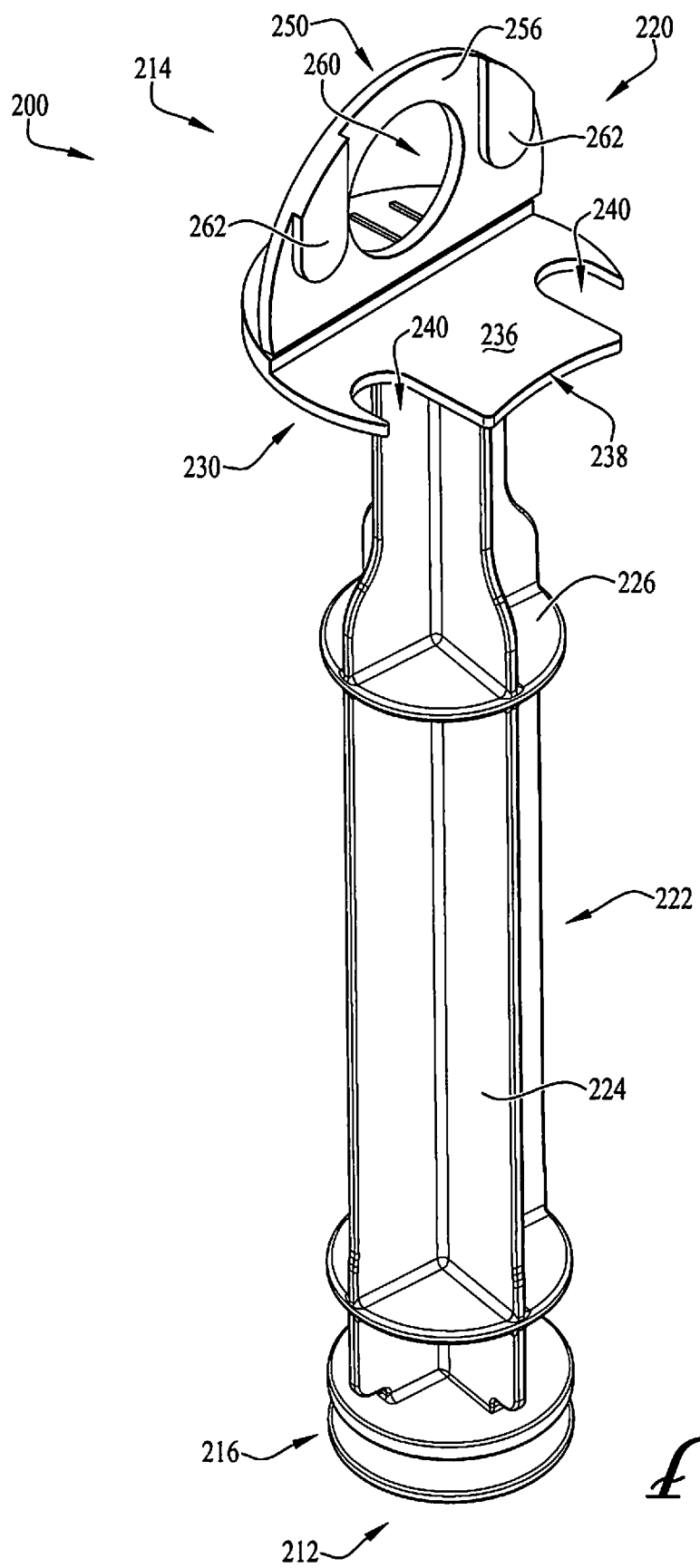
FIG. 12 shows a perspective view of a syringe plunger having a pivoting or hinged pressure flange according to another example embodiment of the present invention, the flange being positioned in an extended or upright configuration.
Figure 13:
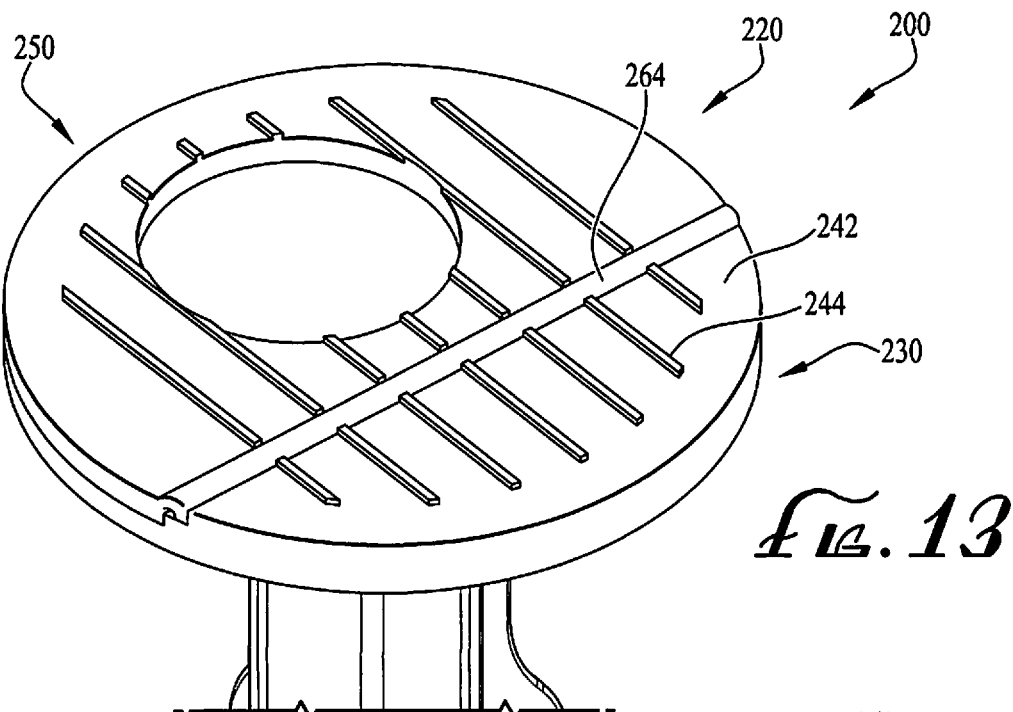
FIG. 13 shows a rear perspective view of the syringe plunger of FIG. 12, and showing the flange being positioned in a flat or collapsed configuration.
Figure 14:
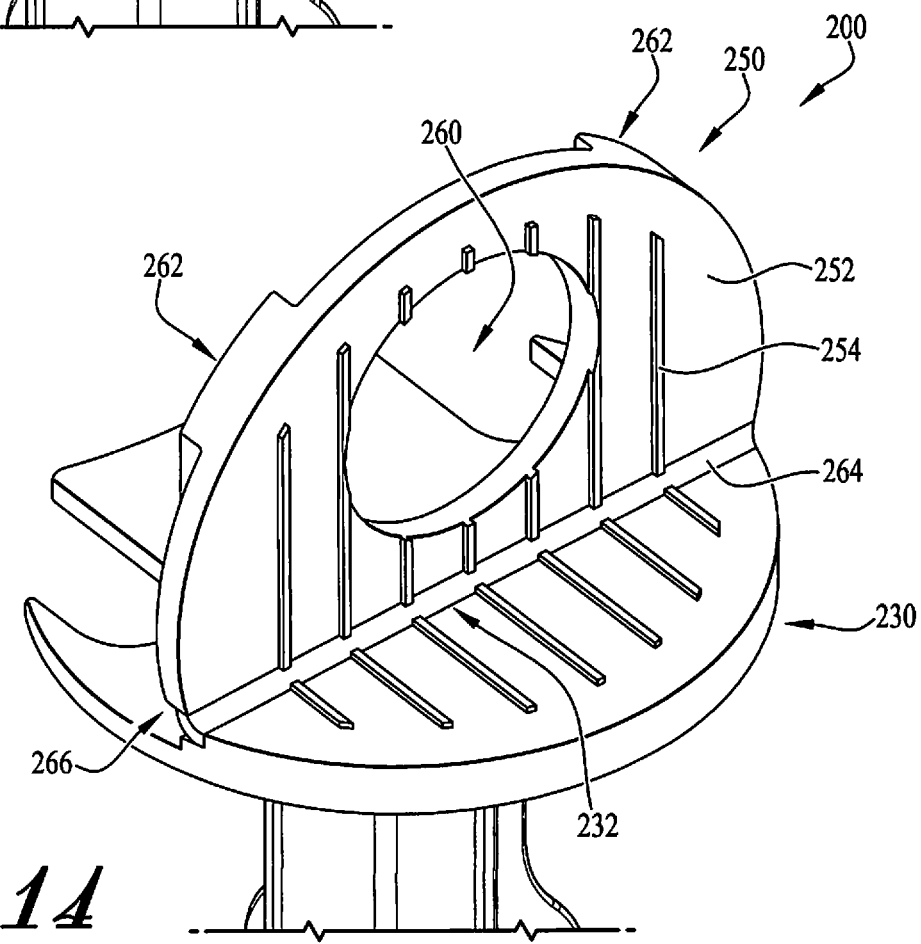
FIG. 14 shows the syringe plunger of FIG. 13, showing the flange being positioned in an extended or upright configuration.

FIGS. 12-14 show a syringe plunger 200 according to another example embodiment of the present invention. As depicted and similarly described above, the contact face 220 is generally disc-shaped and comprises a fixed portion 230 and a flange portion 250, and wherein the flange portion 250 is generally movably mounted to pivot relative to a portion of the fixed portion 230 about a linear pivot edge 232. According to example embodiments, a single living hinge 264 pivotally joins the flange portion 250 to the fixed portion 230 across the width of the contact face 220 of the syringe plunger. In example embodiments, a pair of generally elongate and radiused protrusions 262 of the flange portion are configured for coupling interengagement with engagement receivers 240 of a platform 236 of the fixed portion 130. In example embodiments, the receivers 240 and the protrusions 262 are generally complementary in shape, for example, to provide for fitting interengagement therebetween. In example embodiments, the coupling engagement of the receivers 240 and protrusions 262 is such that at least some interference if provided therebetween, for example to ensure some amount of frictional engagement therebetween generally keeps the flange portion 150 in the collapsed configuration. To move the flange portion to the upright configuration, the user uses a finger or other tool to lift the flange portion relative to the fixed portion. In example embodiments, an end portion 238 of the platform 236 comprises a larger radiused cutout (defined between the two engagement receivers 240) such that a portion of the flange portion 250 overhangs the platform 136 and beyond the end portion 238. Thus, a finger, tool or other device can engage only a portion of the flange portion 250 to move the flange portion 250 from the collapsed configuration to the upright configuration. As similarly described above, an opening can be formed through the flange portion 250 for receiving an IV hook or other hanging support. In example forms, the top surfaces of the fixed portion and the flange portion comprise an array of protruding ribs 244, 254.

Figure 15:
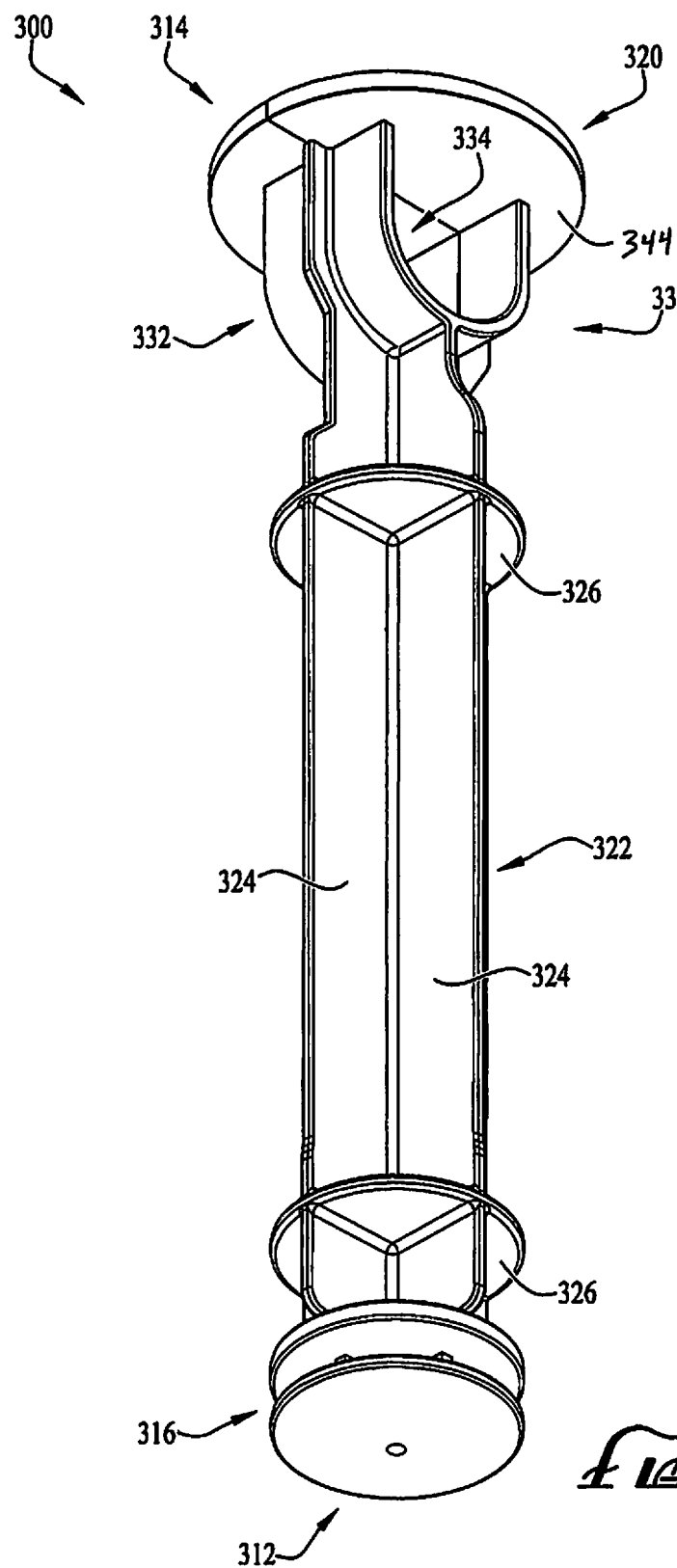
FIG. 15 shows a syringe plunger having an opening or engagement portion according to another example embodiment of the present invention.
Figure 16:
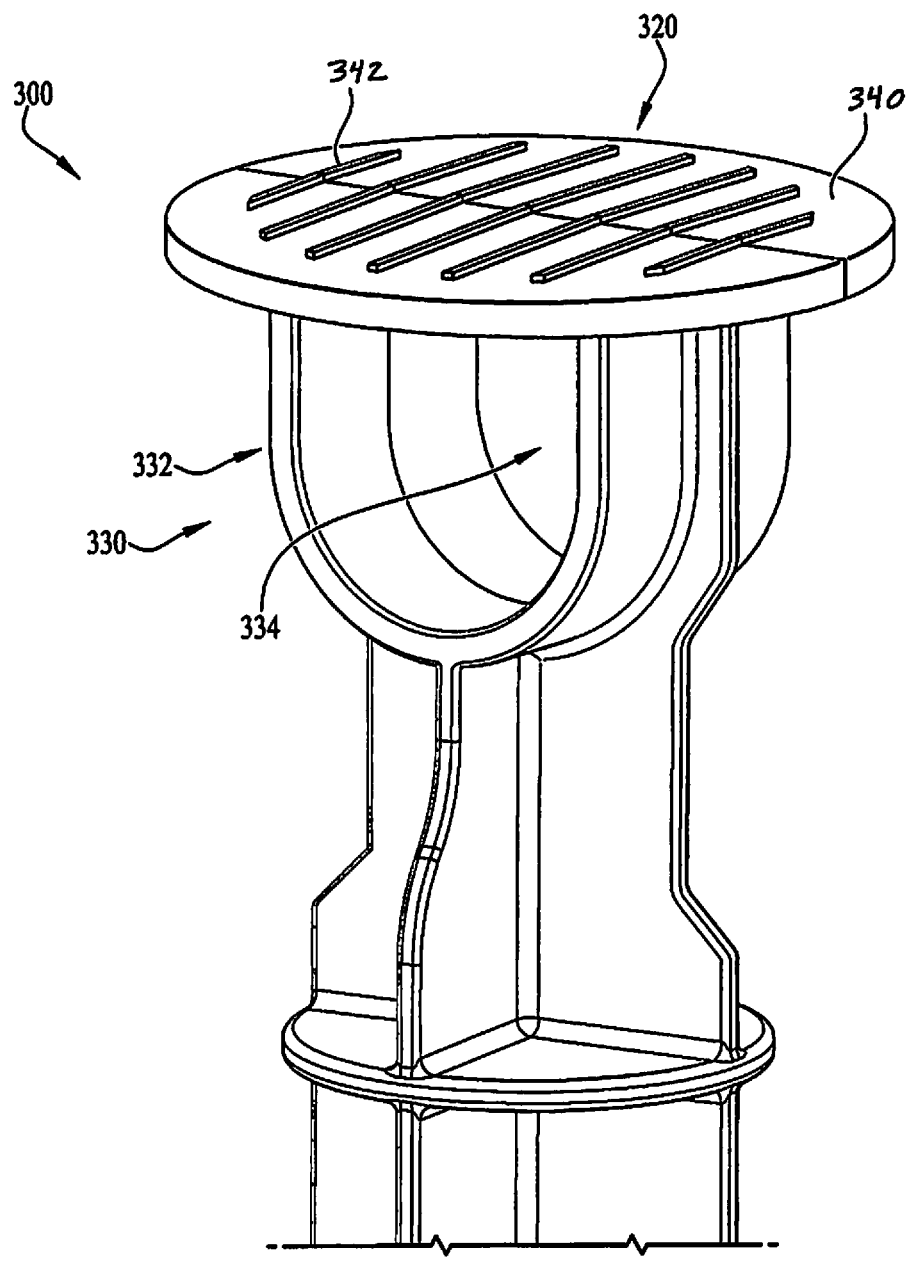
FIG. 16 shows a detailed perspective view of the plunger of FIG. 15.

FIGS. 15-16 show a plunger 300 according to another example embodiment of the present invention. As depicted, the plunger 300 is generally similar to the plungers 10, 100, 200 as described above, for example, which comprises a first or distal end 312 and a second or proximal end 314. The distal end 312 comprises a sealing head 316 for tightly engaging an inner wall of a cavity of a syringe body with a fluid tight seal, and the proximal end 314 comprises a contact face 320 to engage a depressor of a syringe pump or permit user manipulation by hand operation. A main body portion 322 of the plunger 300 generally connects the first end 312 to the second end 314. In example forms, the main body portion 322 generally comprises one or more planar ribs 324 connecting the sealing head 316 to the contact face 320. According to example embodiments, an engagement feature 330 comprising a U-shaped connector or spaced-apart arms 332 connect the main body portion 322 to the contact face 320. According to example embodiments, at least one pass-through or opening 334 is formed within the engagement feature 330 such that an IV hook or other hanging support can engage therewith for hanging the plunger (and syringe attached thereto). In example embodiments, the contact face 320 is generally circular in shape and comprises a generally planar upper surface 340 having a plurality of spaced-apart ribs 342 protruding from the upper surface 340 thereof.

In use, the hinged portion of the contact flange of the syringe plunger is positioned in its flat or retracted position for use with a syringe S when using a syringe pump SP or for manual actuation of the syringe (see FIGS. 17 and 19). In example embodiments, the syringe S comprises a female connector FC (see FIGS. 18-19) in the form of an ENFit (ISO 80369-3 standardized enteral feeding connector) compatible connector or coupling, for example, which can be connected with another ENFit (ISO 80369-3 standardized enteral feeding connector) compatible coupling (which can be connected to a feeding tube FT). In example embodiments, one or more syringe pump clamps C preferably engage the contact flange of the plunger to retain the contact flange up against the driving arm of the pump. As recited above, the thickness T of the contact flange is preferably between about 2-2.25 millimeters, for example, which provides a sufficient thickness for accommodating engagement with the syringe pump clamps C. Alternatively, the hinged portion of the contact flange of the syringe plunger is positioned in its upright or extended position for hanging a syringe S in gravity-feed applications, with an IV hook or other hanging support H extending through the opening in the hinged portion of the contact flange to hang the syringe (see FIG. 18). As described above according to some example embodiments, the syringe S comprises one or more vents V, for example, to utilize the syringe assembly in a gravity-feed system. Further, the vented syringe and plunger of the present invention can be used for manual manipulation or mounted for use with a syringe pump SP.

According to one example form, the packaged plunger (e.g., before being opened by an end user) is generally configured such that the hinged portion is in its flat or retracted position. According to example embodiments, for example in the case when the plunger is molded with the hinged portion in the upright or extended position, the home position of the hinged flange is generally in the flat, retracted position, for example, which can be manipulated with one or more fingers or thumb, and for compatible use with a metering pump. According to some example embodiments, after the manufacture thereof for example in the case where the plunger is plastic injection molded with the flange being in the upright configuration, one or more of the molded plungers can be directed to an assembly line or feeding machine whereby one or more machines and/or operators move the flange portion from the upright configuration to the collapsed configuration, for example, such that the plunger, when assembled individually or with the syringe, is packaged with the flange in the collapsed configuration. Alternatively, in the case where the plunger is assembled with the syringe prior to packaging of the assembly, the plunger with the flange in the upright configuration can be assembled with the syringe and then the assembly can be moved through an automated process whereby a portion of the syringe is captured by a machine or fixture which in turn performs one or more steps to move the flange portion of the contact face from the upright configuration to the collapsed configuration. Optionally, an individual can grab the assembled syringe and plunger and manually move the flange portion from the upright configuration to the collapsed configuration.

Figure 20:
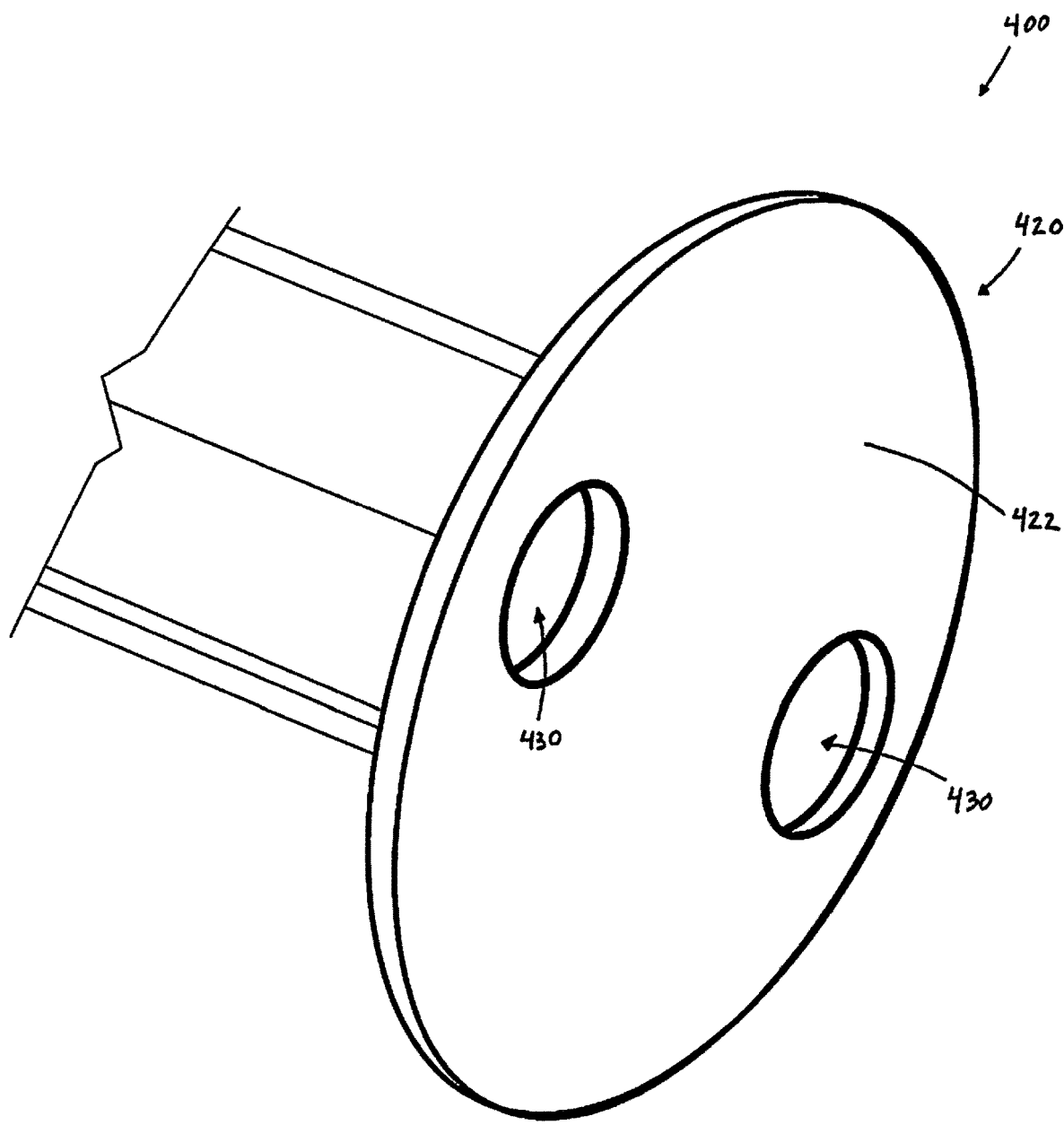
FIG. 20 shows a syringe plunger having a contact face according to another example embodiment of the present invention.

FIG. 20 shows a plunger 400 according to another example embodiment of the present invention. As depicted, the plunger 400 comprises a contact face 420 comprising an upper surface 422 and optionally having a plurality of raised projections or other surface features, for example, as described above with respect to other embodiments of the invention. In example embodiments, the contact face 420 is generally a one piece circular disc having one or more openings 430 extending through the entirety of the contact face 420, for example such that an IV hook or other hanging support H can extend through at least one of the openings 430 to provide for suspending or hanging of the syringe plunger 400 (and syringe barrel S connected with the plunger 400). According to one example embodiment, the openings are generally circular in shape and sized for compatibility with the support H. Optionally, openings of other shapes and sizes can be provided as desired. In other example embodiments, one of the openings can be shaped and sized for compatibility with a first support type, hanger or feature, and the other openings can be sized and shaped for compatibility with another support type, hanger or feature, for example, wherein multiple supportive features can be used to hang the syringe therefrom. Optionally, the one or more openings can be sized and shaped for compatibility with a range of supports is various sizes and shapes.

While the invention has been described with reference to preferred and example embodiments, it will be understood by those skilled in the art that a variety of modifications, additions and deletions are within the scope of the invention, as defined by the following claims.

What is claimed is:

1. A syringe, comprising:
   a syringe barrel; and
   a syringe plunger adapted to advance and retract within the syringe barrel, the syringe plunger comprising a circular, disc-shaped contact flange with a fixed portion having an upper surface and a hinged portion having an upper surface, the disc-shaped contact flange being formed by the upper surface of the fixed portion and the upper surface of the hinged portion, the hinged portion movable between a retracted position in which the upper surface of the fixed portion and the upper surface of the hinged portion respectively are substantially planar relative to each other and an extended position in which the upper surface of the hinged portion extends at an angle relative to the fixed portion, the retracted position adapted for use with a syringe pump or manual actuation, the extended position adapted for hanging from a support,
   wherein the fixed portion comprises a platform and the hinged portion comprises at least one surface configured for coupling interengagement with the platform in the retracted position in which the at least one surface of the hinged portion is positioned above and rests on the platform, and wherein the fixed portion is non-circular shaped.

2. The syringe of claim 1, wherein, when the hinged portion is in the extended position, an opening is defined therethrough for hanging the support.

3. The syringe of claim 1, further comprising at least one vent and an ISO 80369-3 compatible coupling.

4. The syringe of claim 3, wherein the ISO 80369-3 compatible coupling comprises a female connector.

5. The syringe of claim 1, wherein, when the hinged portion is in the retracted position, the contact flange defines a flat profile.

6. The syringe of claim 1, wherein the contact flange comprises a pair of arms and a central member.

7. The syringe of claim 1, wherein the hinged portion comprises a U-shaped portion comprising end extensions and a central connection portion.

8. The syringe of claim 7, wherein each of the end extensions are movably mounted to a pair of arms of the fixed portion by a living hinge.

9. The syringe of claim 1, wherein the contact flange comprises a thickness of between about 2.00 millimeters and 2.25 millimeters.

10. The syringe of claim 1, wherein the syringe plunger comprises a first end, a second end, and a middle body portion extending between the first and second ends, the contact flange being positioned at the first end.

11. The syringe of claim 1, wherein the contact flange comprises one or more surface features.

\* \* \* \* \*

UNITED STATES PATENT AND TRADEMARK OFFICE
CERTIFICATE OF CORRECTION

| | | |
|---|---|---|
| PATENT NO. | : 11,925,791 B2 | Page 1 of 1 |
| APPLICATION NO. | : 16/907777 | |
| DATED | : March 12, 2024 | |
| INVENTOR(S) | : Benjamin M. Davis | |

It is certified that error appears in the above-identified patent and that said Letters Patent is hereby corrected as shown below:

In the Claims

In Claim 1, at Column 10 Line 55, delete "up per" and insert --upper--.

Signed and Sealed this
Tenth Day of December, 2024

Katherine Kelly Vidal
*Director of the United States Patent and Trademark Office*